United States Patent
Boo et al.

(10) Patent No.: US 9,352,169 B2
(45) Date of Patent: May 31, 2016

(54) MEDICAL MASK DEVICE WHICH USES OPTICAL FIBERS

(71) Applicant: KOREA INSTITUTE OF INDUSTRIAL TECHNOLOGY, Cheonan-si, Chungcheongnam-do (KR)

(72) Inventors: Seong Jae Boo, Gyeonggi-do (KR); Hye Jeong Jeong, Gwangju (KR); Seong Min Ju, Gwangju (KR); Won Taek Han, Gwangju (KR)

(73) Assignee: KOREA INSTITUTE OF INDUSTRIAL TECHNOLOGY, Chungcheongnam-do (KR)

( * ) Notice: Subject to any disclaimer, the term of this patent is extended or adjusted under 35 U.S.C. 154(b) by 0 days.

(21) Appl. No.: 14/358,598

(22) PCT Filed: Nov. 16, 2012

(86) PCT No.: PCT/KR2012/009769
§ 371 (c)(1),
(2) Date: May 15, 2014

(87) PCT Pub. No.: WO2013/073913
PCT Pub. Date: May 23, 2013

(65) Prior Publication Data
US 2014/0379053 A1     Dec. 25, 2014

(30) Foreign Application Priority Data
Nov. 18, 2011 (KR) .................. 10-2011-0120748

(51) Int. Cl.
*A61N 5/06* (2006.01)
*A61N 5/067* (2006.01)

(52) U.S. Cl.
CPC ............ *A61N 5/0616* (2013.01); *A61N 5/0625* (2013.01); *A61N 2005/063* (2013.01); *A61N 2005/067* (2013.01); *A61N 2005/0647* (2013.01)

(58) Field of Classification Search
CPC .............. A61N 5/0616; A61N 5/0625; A61N 2005/063; A61N 2005/067; A61N 2005/0647
See application file for complete search history.

(56) References Cited

U.S. PATENT DOCUMENTS

| 5,000,752 | A | * | 3/1991 | Hoskin et al. | 606/9 |
| 5,437,658 | A | * | 8/1995 | Muller et al. | 606/5 |
| 5,944,865 | A | | 8/1999 | Do et al. | |
| 6,104,853 | A | * | 8/2000 | Miyagi et al. | 385/125 |
| 6,743,249 | B1 | * | 6/2004 | Alden | 607/88 |

(Continued)

FOREIGN PATENT DOCUMENTS

| CN | 100531821 C | * | 8/2009 |
| JP | 2004-077658 | | 3/2004 |

(Continued)

OTHER PUBLICATIONS

International Search Report for PCT/KR2012/009769 mailed Mar. 29, 2013.

*Primary Examiner* — Gary Jackson
*Assistant Examiner* — Boniface N Nganga
(74) *Attorney, Agent, or Firm* — Nixon & Vanderhye P.C.

(57) ABSTRACT

Disclosed is a medical mask apparatus using optical fibers which can selectively project a laser beam to an entire treated portion or a local portion of skin. A medical mask apparatus using optical fibers for projecting a fine laser beam to the skin to activate skin cells and expedite circulation of blood in the skin is provided.

4 Claims, 6 Drawing Sheets

(56) References Cited

U.S. PATENT DOCUMENTS

| | | |
|---|---|---|
| 7,081,128 B2 * | 7/2006 | Hart et al. .................. 607/89 |
| 7,228,035 B2 | 6/2007 | Noguchi et al. |
| 2006/0018600 A1 | 1/2006 | Noguchi et al. |
| 2009/0187170 A1 * | 7/2009 | Auld et al. .................. 606/4 |
| 2011/0040355 A1 * | 2/2011 | Francis ...................... 607/88 |
| 2011/0152978 A1 * | 6/2011 | Dacey et al. ............... 607/92 |
| 2012/0172951 A1 * | 7/2012 | Choi ........................... 607/91 |
| 2014/0350643 A1 * | 11/2014 | Pepitone et al. ............ 607/89 |

FOREIGN PATENT DOCUMENTS

| | | |
|---|---|---|
| JP | 2006-014776 | 1/2006 |
| KR | 10-0217716 | 6/1999 |
| KR | 10-0939665 | 1/2010 |
| KR | 10-1074882 | 10/2011 |

* cited by examiner

PRIOR ART

MEDICAL MASK DEVICE WHICH USES OPTICAL FIBERS

This application is the U.S. national phase of International Application No. PCT/KR2012/009769 filed 16 Nov. 2012 which designated the U.S. and claims priority to KR 10-2011-0120748 filed 18 Nov. 2011, the entire contents of each of which are hereby incorporated by reference.

BACKGROUND OF THE INVENTION

1. Field of the Invention

The present invention relates to a medical mask apparatus using optical fibers, and more particularly to a medical mask apparatus using optical fibers which allows easy projection of a laser beam to a treated portion of a face.

2. Description of the Prior Art

In general, the optical fiber is an optical fiber which totally reflects light passing through a central portion of glass by making a refractive index of the central portion of the glass high and a refractive index of an outer portion low. The optical fiber loses a very small amount of energy and thus a loss rate of transmitted and received data is low and is rarely influenced by an external environment.

The optical fiber has been applied to various fields recently, and in particular, laser apparatuses using optical fibers are utilized for various purposes in various fields such as industries, medicine, communications, the military, measurements, and displays. In particular, the application ranges of laser technologies are gradually increasing in the medical fields such as ophthalmology, dentistry, surgery, and skin treatments.

Since laser projection using optical fibers is made as laser oscillations are performed in an optical fiber itself, a volume to a surface area of the laser oscillating rod becomes maximal so that laser oscillation may be performed stably. Accordingly, lowering of laser oscillation efficiency due to loss of heat can be minimized.

Meanwhile, a laser apparatus (hereinafter, referred to as 'a medical laser apparatus') according to the related art applied to the medical fields projects a laser beam of a fine wavelength of 400 nm to 900 nm, and the projected laser beam penetrates deeply into the skin so that skin makeup can be improved by expediting circulation of blood in the skin.

Since the medical laser apparatus should secure low electric power and thermoelectric stability, energy conversion efficiency of an optical fiber laser is unstable when a laser oscillating optical fiber is utilized, and the utilization of the optical fiber laser is restrictive due to photo-darking caused by electronic excitements, which requires an additional apparatus.

Further, the medical laser apparatus according to the related art recently has been modified in various forms to be conveniently used, and an example thereof includes a makeup mask by which a laser beam may be projected.

FIG. 1 is a schematic diagram showing a makeup mask according to the related art. As shown in FIG. 1, the makeup mask includes a fabric mask body 10 including optical fibers 11 connected to a plurality of light sources 20.

The makeup mask according to the related art covers a portion of a face. Meanwhile, the light sources 20 used here employ medical laser modules, and use large diameter optical fibers of 200 μm to 800 μm instead of communication optical fibers (generally, around 125 μm) (aim to secure outputs).

Thus, it is impossible to minutely project laser beams to the skin through large diameter optical fibers.

Further, the optical fibers 11 applied to the makeup mask according to the related art employ a separate switching means to control optical outputs of ends of the optical fibers 11.

However, when the medical laser modules (including the makeup mask according to the related art) according to the related art separately include a switching means, they occupy a relatively large portion of the volume of the apparatus, making it difficult to miniaturize the apparatus and increasing manufacturing costs.

SUMMARY OF THE INVENTION

The present invention has been made in an effort to solve the above-mentioned problems, and it is an object of the present invention to provide a medical mask apparatus using optical fibers by which light can be finely projected to a treated portion and laser surgeries can be selectively controlled according to a local treated portion due to a simplified structure thereof.

In order to accomplish this object, there is provided a medical mask apparatus using optical fibers for projecting a fine laser beam to the skin to activate skin cells and expedite circulation of blood in the skin, the medical mask apparatus including: a laser light source generator for generating and supplying a laser beam having a predetermined wavelength band; a plurality of optical fibers branched from the laser light source generator; and a mask body having a cover portion having a predetermined area such that the cover portion covers a portion of a face and in which a portion of a distal end of the optical fiber is exposed along the entire cover, wherein an electro-optic material is coated on an output end of the optical fiber such that an output of the output end of the optical fiber is controlled by an external electrical signal, and the output end of the optical fiber has a diameter smaller than that of an input end of the optical fiber connected to the laser light source generator such that fine projection is allowed.

The optical fiber includes a core and a cladding, the core is tapered such that a diameter of an output end of the core is 70±5 μm when a diameter of an input end of the core is 550±55 μm, and the cladding is tapered such that a diameter of an output end of the cladding is 80±10 μm when a diameter of an input end of the cladding is 600±60 μm.

The electro-optic material is one selected from the group consisting of aluminum, copper, and silver.

The medical mask apparatus further includes an optical fiber connector for fixing the optical fiber to the mask body, and the optical fiber connector has through-holes whose diameters are different such that the input end and the output end of the optical fiber having different diameters pass through the through-holes.

The optical fiber connector includes: a first through-hole formed at a tip end of the optical fiber connector such that the input end of the optical fiber is inserted into the first through-hole; a first through-hole formed at a distal end of the optical fiber connector such that the output end of the optical fiber is inserted into the second through-hole; and an intermediate connecting portion connecting the first through-hole and the second through-hole and having a tapered inner surface.

The optical fiber forms a plurality of channels by grouping a plurality of objects and projection of light to the optical fibers is controlled for groups by applying an electrical signal to the channels.

The mask body includes a first cover portion and a second cover portion formed at opposite sides of the mask body while a connector is located therebetween, and wherein a first projection area and a second projection area having a plurality of exposure holes with a predetermined area through which output ends of the optical fibers are exposed are formed inside the first cover portion and the second cover portion.

According to the present invention, since an output portion of an optical fiber having a large diameter according to the related art is tapered, light can be finely projected, improving efficiency of a surgery. Further, since projection of light is controlled for channels by coating an electro-optic material at a terminal end of an optical fiber, surgeries for a local portion of a face can be selectively performed, the apparatus can be simplified, and manufacturing costs can be lowered.

BRIEF DESCRIPTION OF THE DRAWINGS

The above and other objects, features and advantages of the present invention will be more apparent from the following detailed description taken in conjunction with the accompanying drawings, in which.

DETAILED DESCRIPTION OF THE EXEMPLARY EMBODIMENTS

Hereinafter, an exemplary embodiment of the present invention will be described in detail with reference to the accompanying drawings.

Figure 1:
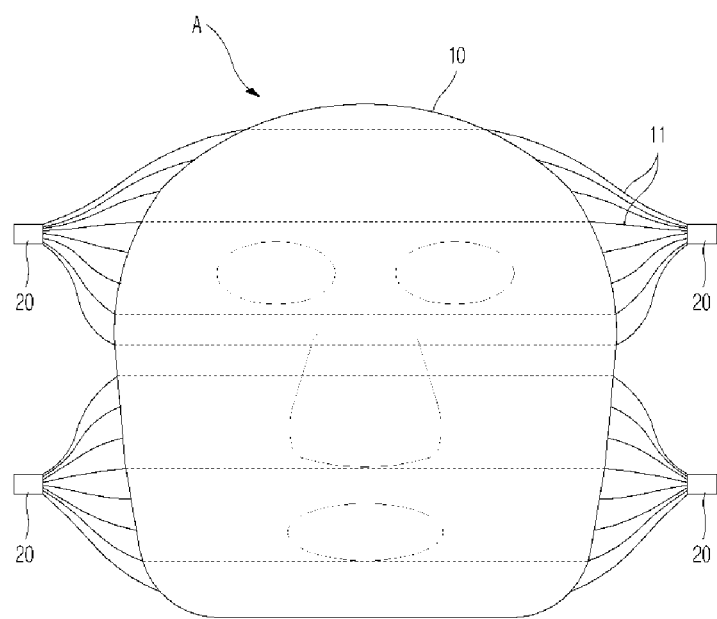
FIG. 1 is a schematic diagram showing a makeup mask according to the related art.
Figure 2:
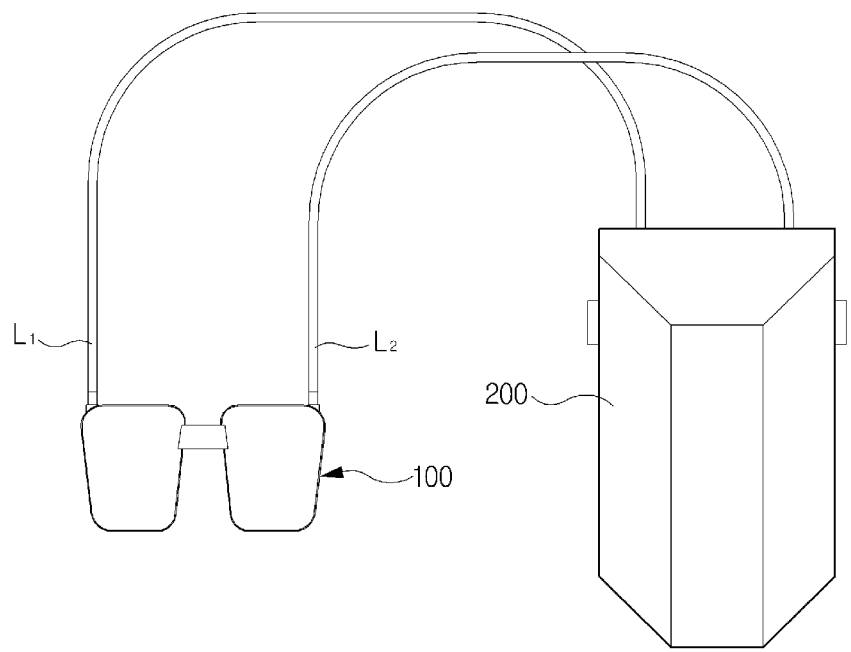
FIG. 2 is a schematic diagram of a medical mask apparatus using optical fibers according to an embodiment of the present invention.
Figure 3:
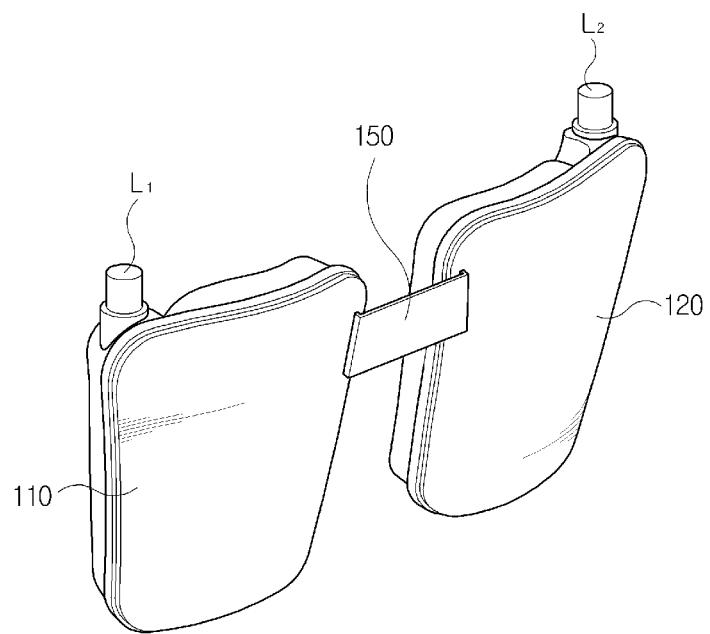
FIG. 3 is a perspective view of a mask body of the medical mask apparatus using optical fibers according to the embodiment of the present invention.
Figure 4:
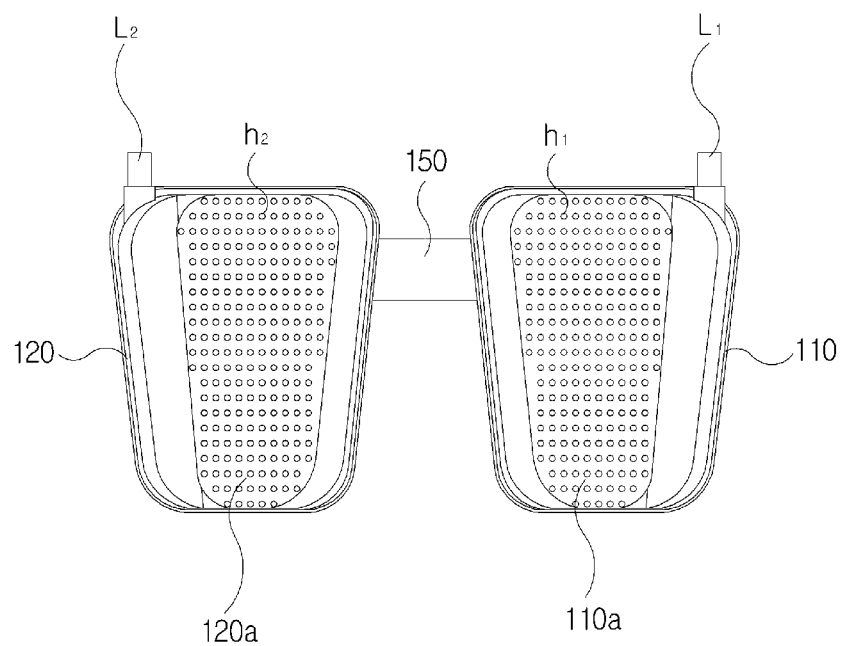
FIG. 4 is a schematic diagram showing an inside of a mask body of the medical mask apparatus using optical fibers according to the embodiment of the present invention.
Figure 5:
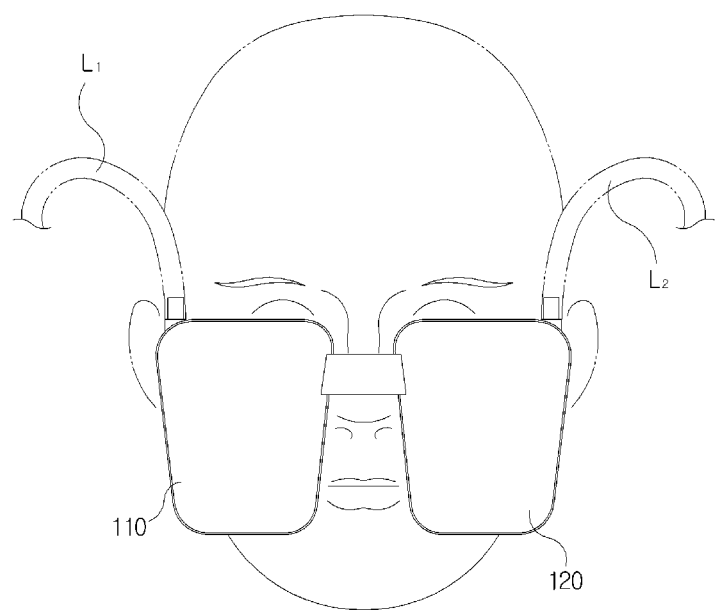
FIG. 5 is a view showing an in-use state of the the medical mask apparatus using optical fibers according to the embodiment of the present invention.

FIG. 2 is a schematic diagram of a medical mask apparatus using optical fibers according to an embodiment of the present invention. FIG. 3 is a perspective view of a mask body of the medical mask apparatus using optical fibers according to the embodiment of the present invention. FIG. 4 is a schematic diagram showing an inside of a mask body of the medical mask apparatus using optical fibers according to the embodiment of the present invention. FIG. 5 is a view showing an in-use state of the the medical mask apparatus using optical fibers according to the embodiment of the present invention.

As shown in FIG. 2, the medical mask apparatus according to the present invention includes a mask body 100 connected to a laser light source generator 200 through optical cables L1 and L2.

The laser light source generator 200 may secure a constant optical output by applying a general solid laser module or a semiconductor laser module. A large diameter optical fiber of 200 μm to 800 μm is applied to the optical cables L1 and L2 connected to the laser light source generator 200 to secure a constant optical output.

As shown in FIGS. 3 to 5, in the mask body 100, a first cover portion 110 and a second cover portion 120 may be connected to each other via a connector 150. Accordingly, the mask body 100 may easily cover facial surfaces (cheeks) of the user (see FIG. 5). Output ends of a plurality of optical fibers 300 branched from the optical cables L1 and L2 are distributed on entire surfaces of the cover portions 110 and 120 while being exposed. In detail, as shown in FIG. 4, projection areas 110a and 120a in which a plurality of exposure holes h1 and h2 are formed to have a predetermined area are formed in eye contact areas of the mask body 100, and the output ends of the optical fibers 300 are provided in the exposure holes h1 and h2 while being exposed. Accordingly, laser beams may be widely projected to local portions of the face.

The optical fiber 300 applied to the medical mask apparatus according to the present invention is configured such that an output end of the optical fiber 300 is tapered to minutely project light to the skin, which will be described in detail.

Figure 6:
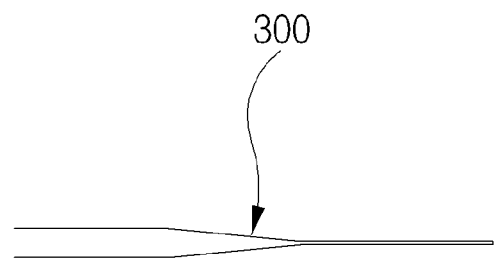
FIG. 6 is a view showing an optical fiber of the the medical mask apparatus using optical fibers according to the embodiment of the present invention.
Figure 7:
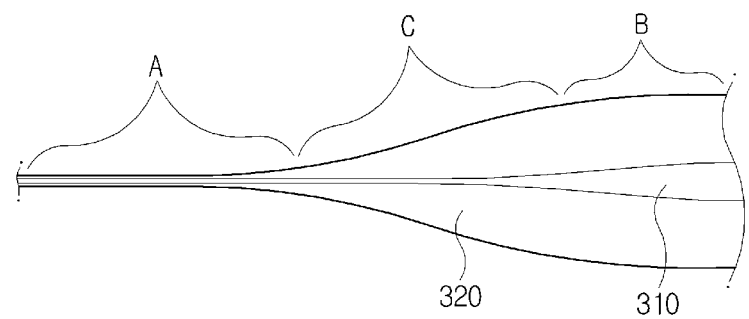
FIG. 7 is a schematic diagram showing an optical fiber of the the medical mask apparatus using optical fibers according to the embodiment of the present invention.

FIG. 6 is a view showing an optical fiber of the the medical mask apparatus using optical fibers according to the embodiment of the present invention. FIG. 7 is a view showing an optical fiber of the the medical mask apparatus using optical fibers according to the embodiment of the present invention.

As shown in FIGS. 6 and 7, a terminal end of the optical fiber 300 applied to the mask apparatus according to the present invention is tapered to be minutely processed easily.

An output end of an optical fiber of a large diameter (200 μm to 800 μm) according to the related art may become thinner by tapering the output end of the optical fiber through thermal processing. That is, the optical fiber 300 generally includes a core 310 and a cladding 320, and according to the present invention, the optical fiber 300 is tapered through thermal processing such that a diameter of an output end A of the core 310 is 70±5 μm when a diameter of an input end B of the core 310 is 550±55 μm and a diameter of an output end A of the cladding 320 is 80±10 μm when a diameter of an input end B of the cladding 320 is 600±60 μm. Accordingly, a tapered portion C may be formed between the output end A and the input end B.

By forming the optical fiber 300 in this way, a light source output from the laser light source generator 20 of a high output may be concentrated to the output end A of a plurality of tapered optical fibers 300 to easily penetrate into the skin tissues.

Then, the light output from the optical cables L1 and L2 of the laser light source generator 200 is branched (through a distributer in the light source generator) to be projected, and a local portion of skin needs to be treated according to an occasion.

Thereto, according to the present invention, a method of coating an electro-optic material and controlling optical output is employed at an output end A of the optical fiber 300. In detail, an electro-optic material is a material such as Au, Ag, or Cu, and the electro-optic material may absorb light according a wavelength of the light. The electro-optic material uses a property (light absorption characteristics) of the electro-optic material, and although a beam of a specific laser wavelength passes through the electro-optic material in a general situation, the electro-optic material absorbs a beam of a laser wavelength as a light absorbing wavelength band is changed if an electrical signal is applied from the outside to the electro-optic material so that emission of a laser beam is interrupted (light is absorbed).

According to the present invention, the electro-optic material is coated on the optical fiber 300, and a local control of the optical fiber 300 distributed in the entire mask body 100 is allowed (that is, projection of a laser beam to a predetermined area may be interrupted). In addition, the optical fibers 300 are grouped to form a plurality of channels, and an individual control (controls for groups) may be allowed by applying an electrical signal to the channels.

Figure 8:
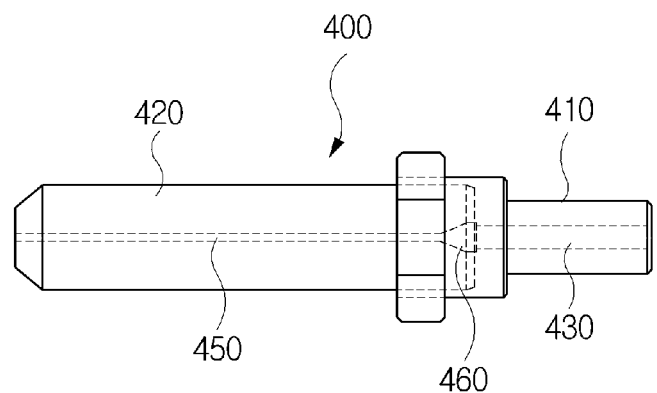
FIG. 8 is a schematic diagram showing an optical fiber connector of the the medical mask apparatus using optical fibers according to the embodiment of the present invention.

FIG. 8 is a schematic diagram showing an optical fiber connector of the the medical mask apparatus using optical fibers according to the embodiment of the present invention. As shown in FIG. 8, the medical mask apparatus may include an optical fiber connector 400 for fixing the optical fiber 300 to the mask body 100. That is, the optical fiber connector 400 functions to extract the optical fibers 300 fixed to an inside of the mask body 100 through the exposure holes h1 and h2 such that the output ends of the optical fibers 300 are exposed through the plurality of exposure holes h1 and h2 formed in projection areas 110a and 120a of the first cover portion 110 and the second cover portion 120.

The optical fiber connector 400 may be applied in the form of a subminiature connector (SMA), and the SMA connector method according to the related art is used to introduce a light source of a laser module of a high output into the optical fiber 300.

In the optical fiber connector 400 applied to the present invention, the diameters of the through-holes 430 and 450 are made differently such that the input end B and the output end A of different optical fibers 300 pass through the through-holes 430 and 450 while the optical fiber connector 400 takes the form of an SMA connector.

That is, optical fibers 300 having different diameters may be easily extracted to the outside while the optical fibers 300 are fixed to the mask body 100 by providing the optical fiber connector 400 having an input unit 410 for introducing an input end of the optical fiber 300 of a larger diameter (200 μm to 800 μm) and an output unit 420 through which the tapered output end A passes. Then, an intermediate connecting portion 460 where the tapered portion C of the optical fiber 300 may be formed between the input unit 410 and the output unit 420.

In this way, according to the present invention, since an output end of the optical fiber 300 into which a light source output from the laser light source generator 200 is introduced is tapered such that light is projected to a terminal end of the optical fiber 300, a laser beam may be minutely projected to the skin and thus an efficiency of the laser surgery may be improved.

Further, the present invention coats an electrical coating material on the output end of the optical fiber 300 to control projection of laser beams for channels, simplifying the apparatus and lowering manufacturing costs while allowing a selective surgery for a local portion.

Although a specific embodiment of the present invention has been illustrated and described, the present invention is not limited to the embodiment, but it will be appreciated by those skilled in the art to which the present invention pertains that the present invention can be variously modified without departing from the spirit of the present invention which is claimed in the claims.

What is claimed is:

1. A medical mask apparatus using optical fibers for projecting a fine laser beam to the skin to activate skin cells and expedite circulation of blood in the skin, the medical mask apparatus comprising:
    a laser light source generator for generating and supplying a laser beam having a predetermined wavelength band;
    a plurality of optical fibers branched from the laser light source generator; and
    a mask body having a cover portion having a predetermined area such that the cover portion covers a portion of a face and in which a portion of distal ends of the optical fibers are exposed along the entire cover,
    optical fiber connectors fixing the optical fibers to the mask body, the optical fiber connectors having a through-hole wherein a first portion of the through-hole at an input end of the connector has a first diameter, a second portion of the through-hole at a distal end of the connector has a second diameter, and an intermediate connecting portion of the through-hole between said first portion and said second portion has a tapered diameter, the input end of the optical fibers being inserted into the first portion and the output end of the optical fibers being inserted into the second portion;
    wherein an electro-optic material is coated on output ends of the optical fibers such that an output of the output ends of the optical fibers is controlled by an external electrical signal, and
    the output ends of the optical fibers have a diameter smaller than that of an input end of the optical fibers connected to the laser light source generator such that fine projection is allowed,
    said optical fibers including a core and a cladding, the core being tapered such that a diameter of an output end of the core is 70±5 μm when a diameter of an input end of the core is 550±55 μm, and the cladding being tapered such that a diameter of an output end of the cladding is 80±10 μm when a diameter of an input end of the cladding is 600±60 μm.

2. The medical mask apparatus of claim 1, wherein the electro-optic material is selected from the group consisting of aluminum, copper, and silver.

3. The medical mask apparatus of claim 1, wherein the optical fibers are grouped to form a plurality of channels and projection of light to the optical fibers is controlled by applying an electrical signal to the channels.

4. The medical mask apparatus of claim 1, wherein the mask body comprises a first cover portion and a second cover portion formed at opposite sides of the mask body while a connector is located therebetween, and wherein a first projection area and a second projection area having a plurality of exposure holes with a predetermined area through which output ends of the optical fibers are exposed are formed inside the first cover portion and the second cover portion.

* * * * *